(12) United States Patent
Lai

(10) Patent No.: US 7,252,506 B2
(45) Date of Patent: Aug. 7, 2007

(54) ARCH MEMBER FOR AN ORTHODONTIC BRACE

(75) Inventor: Ming-Lai Lai, Arcadia, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 52 days.

(21) Appl. No.: 10/865,148

(22) Filed: Jun. 10, 2004

(65) Prior Publication Data

US 2005/0277083 A1    Dec. 15, 2005

(51) Int. Cl.
*A61C 3/00* (2006.01)
(52) U.S. Cl. ........................................ 433/20
(58) Field of Classification Search ................ 433/20, 433/18, 22
See application file for complete search history.

(56) References Cited

U.S. PATENT DOCUMENTS

| | | | |
|---|---|---|---|
| 2,821,020 A | 1/1958 | Brusse | |
| 3,043,007 A | 7/1962 | Wallshein | |
| 3,593,421 A * | 7/1971 | Brader | 433/21 |
| 4,248,588 A | 2/1981 | Hanson | |
| 4,479,779 A | 10/1984 | Wool | |
| 4,492,573 A | 1/1985 | Hanson | |
| 4,585,414 A | 4/1986 | Kottemann | |
| 4,659,310 A | 4/1987 | Kottemann | |
| 4,712,999 A | 12/1987 | Rosenberg | |
| 4,717,341 A * | 1/1988 | Goldberg et al. | 433/9 |
| 4,731,018 A | 3/1988 | Adell | |
| 4,850,865 A | 7/1989 | Napolitano | |
| 4,897,036 A | 1/1990 | Kesling | |
| 5,017,133 A | 5/1991 | Miura | |
| 5,137,446 A | 8/1992 | Yamauchi et al. | |
| 5,174,753 A | 12/1992 | Wool | |
| 5,238,404 A | 8/1993 | Andreiko | |
| 5,259,760 A | 11/1993 | Orikasa | |
| 5,295,886 A * | 3/1994 | Wildman | 433/24 |
| 5,456,599 A | 10/1995 | Hanson | |
| 5,468,147 A | 11/1995 | Yao | |
| 5,474,447 A | 12/1995 | Chikami et al. | |
| 5,683,245 A | 11/1997 | Sachdeva et al. | |
| 5,711,666 A | 1/1998 | Hanson | |
| 6,095,809 A | 8/2000 | Kelly et al. | |
| 6,302,688 B1 | 10/2001 | Jordan et al. | |
| 6,315,553 B1 * | 11/2001 | Sachdeva et al. | 433/24 |
| 6,582,226 B2 | 6/2003 | Jordan et al. | |

\* cited by examiner

*Primary Examiner*—John J Wilson
(74) *Attorney, Agent, or Firm*—James D. Christoff

(57) ABSTRACT

A brace for an orthodontic patient includes a set of appliances fixed to the patient's teeth and an arch member connected to the appliances. The arch member has a series of notches presenting narrowed sections, and the narrowed sections are received in slots of corresponding appliances. As such, the sections of the arch member in regions between adjacent notches are not constrained by the shape of the slots of the appliances. Preferably, the arch member is comprised of an aesthetic polymeric material such as a stain-resistant transparent or translucent material.

10 Claims, 3 Drawing Sheets

ARCH MEMBER FOR AN ORTHODONTIC BRACE

BACKGROUND OF THE INVENTION

1. Field of the Invention

This invention relates to an arch member for use in orthodontic treatment. The arch member and a set of orthodontic appliances comprise an orthodontic brace that is useful for correcting a malocclusion.

2. Description of the Related Art

Orthodontic treatment involves movement of a dental patient's teeth to improved positions in proper alignment with each other. Orthodontic treatment can greatly enhance the patient's facial appearance, especially in regions near the front of the oral cavity. Orthodontic treatment can also improve the function of the teeth so that the opposing teeth work better with each other during mastication.

One type of common orthodontic treatment includes the use of a set of tiny appliances known as brackets. Each bracket has a slot and is affixed to one of the patient's anterior, cuspid or bicuspid teeth. Conventionally, a thin, resilient metallic archwire is received in the slots of the brackets and forms a track to guide movement of the teeth to desired positions. Ends of the archwire are often received in buccal tube appliances that are affixed to the patient's molar teeth.

Today, the archwire slot of orthodontic appliances is commonly available in a height of either of two sizes: a 0.018 in. (0.46 mm) slot size and a 0.022 in. (0.56 mm) slot size. The appliances with the larger archwire slot are chosen by practitioners that prefer to use a larger, stiffer archwire. A stiffer archwire has the capability of exerting more force on the patient's teeth so that the length of treatment time is not unduly extended. However, many practitioners prefer to use appliances with smaller archwire slots in combination with smaller archwires that are less stiff, and find that the results at the conclusion of treatment are satisfactory.

Another type of common orthodontic treatment system involves a set of custom-made plastic positioners or trays such as the "Invisalign" brand trays sold by Align Technology of Santa Clara, Calif. Each tray is made to move the teeth a relatively small, incremental distance toward desired final positions. The trays are made of a plastic material with sufficient resiliency to urge the teeth toward the positions defined by the tray when the tray is relaxed.

Regardless of which orthodontic treatment system is employed, it is often desirable to manufacture the components of the system from a material that is aesthetically pleasing so that the patient's facial appearance is not unduly affected during the course of treatment. For example, components of the treatment system may be made of a transparent or translucent material that enables the color of the patient's teeth to be visible when viewed through the components. As another alternative, the components may be made of a material that has a color that matches the color of the patient's dentition.

SUMMARY OF THE INVENTION

The present invention relates to an arch member for an orthodontic brace. The arch member has a series of notches that accommodate appliances fixed to the patient's teeth. As a consequence, the cross-sectional shape of the arch member at various locations along its length is not necessarily limited to the confines of the archwire slot that is provided in the appliances.

For example, the arch member may have a larger cross-sectional area in regions between each appliance. Such construction enables the stiffness of the arch member to be greater in such regions than what might be otherwise provided. This increase in stiffness optionally permits the arch member to be made of materials that might otherwise be deemed unsatisfactory for moving teeth to desired positions.

For instance, the arch member can be made of a stain-resistant transparent or translucent polymer having aesthetic characteristics. Optionally, fibers can be embedded in the polymer to increase its strength. As an additional option, the polymer arch member may be formed to a certain configuration that urges teeth to incremental positions that are intermediate the initial position of the teeth and the final, desired positions of the teeth, somewhat similar to a method of treatment using custom-made positioners or trays.

In more detail, the present invention is directed in one aspect to an arch member for an orthodontic brace. The arch member comprises an elongated body having an overall, generally "U"-shaped configuration. The body has a plurality of notches that are spaced apart from each other along the length of the body. The centerline spacing between adjacent notches generally corresponds to the centerline distance between corresponding, adjacent teeth of the dental arch.

The present invention is also directed to a brace for an orthodontic patient in accordance with another aspect of the invention. The brace comprises a set of orthodontic appliances, each of which is connected to a tooth of the patient's dental arch. The brace also includes an arch member that comprises an elongated body with an overall, generally "U"-shaped configuration. The body has a plurality of notches that are spaced apart from each other along the length of the body, and at least some of the appliances are coupled to the body in locations corresponding to the notches.

These and other features of the invention are described in more detail in the paragraphs that follow and are illustrated in the accompanying drawings.

DETAILED DESCRIPTION OF THE PREFERRED EMBODIMENTS

Figure 1:
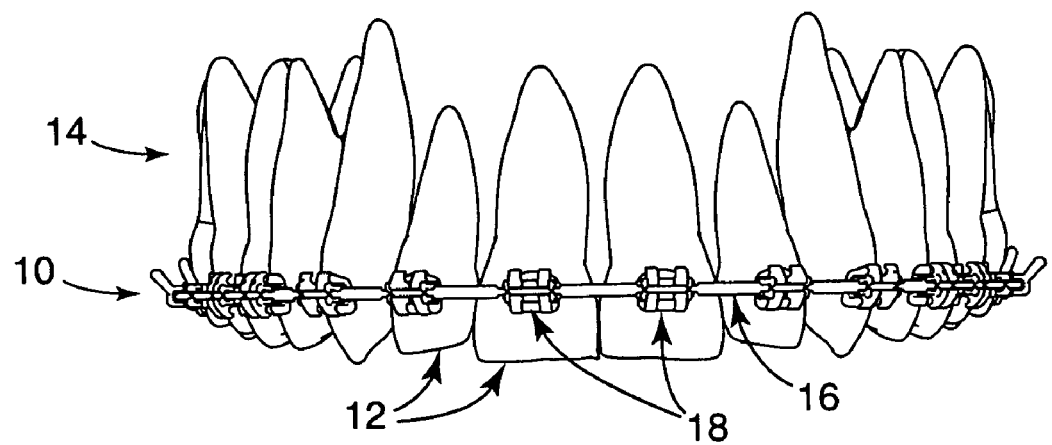
FIG. 1 is a front elevational view of an exemplary upper dental arch of a patient undergoing orthodontic treatment, wherein a brace according to one embodiment of the invention of the invention is connected to various teeth of the dental arch and comprises a set of orthodontic appliances and an arch member coupled to the appliance.
Figure 2:
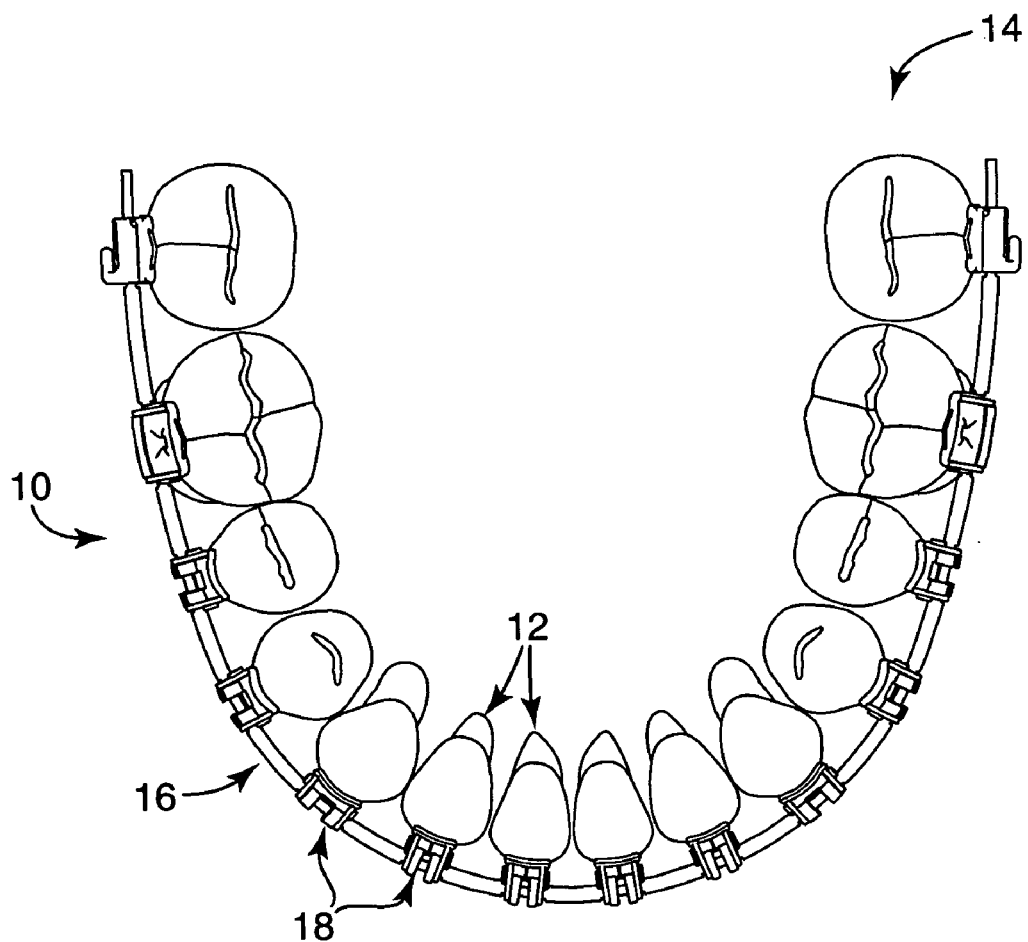
FIG. 2 is a bottom view of the dental arch and brace illustrated in FIG. 1.

An orthodontic brace according to one embodiment of the present invention is illustrated in FIG. 1 and is broadly designated by the numeral 10. The brace is connected to teeth 12 that are located along a dental arch 14 of an exemplary patient that is undergoing orthodontic treatment. The dental arch 14 shown in FIG. 1 is the upper dental arch of the patient, and it should be understood in this regard that the patient's lower dental arch may be treated with a similar brace as well.

The brace 10 includes an arch member 16 as well as a set of orthodontic appliances 18. Each of the appliances 18 is fixed to a corresponding one of the patient's teeth 12. In turn, the arch member 16 is connected to the appliances 18. The appliances may be orthodontic brackets, buccal tubes or any other type of appliance that has a passage or slot for receiving the arch member 16.

Figure 7:
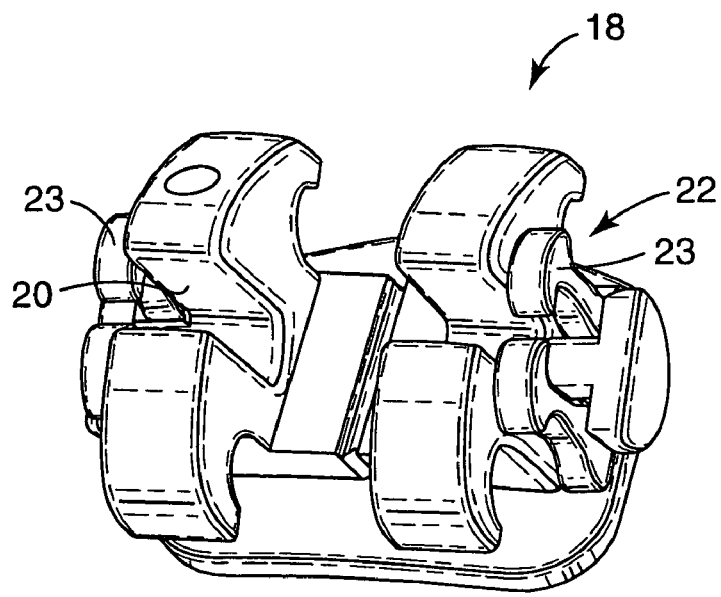
FIG. 7 is an enlarged perspective view of one of the orthodontic appliances depicted in FIGS. 1, 2 and 6.

An example of a suitable appliance 18 is illustrated in enlarged view in FIG. 7. The illustrated appliance 18 is known as a "self-ligating" bracket and is similar to the appliances described in U.S. Pat. Nos. 6,302,688 and 6,582,226, both of which are hereby expressly incorporated by reference herein. The appliance 18 has an elongated archwire slot 20 that extends across the appliance 18 in a generally mesial-distal direction.

The exemplary self-ligating appliance 18 illustrated in FIG. 7 has a latch 22 for releasably retaining an archwire or arch member (such as arch member 16) in the archwire slot 20. In this embodiment, the latch 22 comprises a pair of resilient clips 23 having a generally "C"-shaped configuration. Preferably, the clips 23 are sufficiently flexible to enable the practitioner to insert the arch member 16 in the archwire slot 20 by pressing the same in a lingual direction such that the sides of the clips 23 deflect outwardly and away from each other. Once the arch member 16 is clear of the outer arm portions of the clips 23 and located in the archwire slot 20, the sides of the clips 23 self-deflect and spring back toward each other to their normal closed orientation in order to retain the arch member 16 in the archwire slot 20.

Preferably, the sides of the clips 23 deflect outwardly in enable the latch 22 to assume a slot-open orientation and release the arch member 16 from the archwire slot 20 whenever the force exerted by the arch member 16 on the appliance 18 exceeds a certain minimum value. This minimum value is sufficiently high to prevent the arch member 16 from unintentionally releasing from the archwire slot 20 during the normal course of orthodontic treatment. As such, the arch member 16 can exert forces on the appliance 18 sufficient to carry out the intended treatment program and move the associated tooth as desired. Further details and additional options for the appliance 18 are set out in the aforementioned U.S. Pat. Nos. 6,302,688 and 6,582,226.

Other types of self-ligating appliances are also possible. For example, the appliance 18 may be identical or similar to the self-ligating appliances described or referenced in U.S. Pat. Nos. 4,248,588, 4,492,573, 4,712,999 and 5,711,666.

As another alternative, the appliance may be a bracket that is not a self-ligating bracket. For example, the appliance may lack a latch and be provided with two or more projections known as "tiewings" that are located on opposite sides of the archwire slot. In practice, the arch member 16 is retained in the archwire slot of such a bracket by extending a ligature around the tiewings as well as over the arch member 16 in order to retain the latter in the archwire slot. Suitable ligatures include tiny, elastomeric O-ring ligatures as well as sections of small-diameter metallic wire with ends that are twisted together to form a loop.

Figure 3:
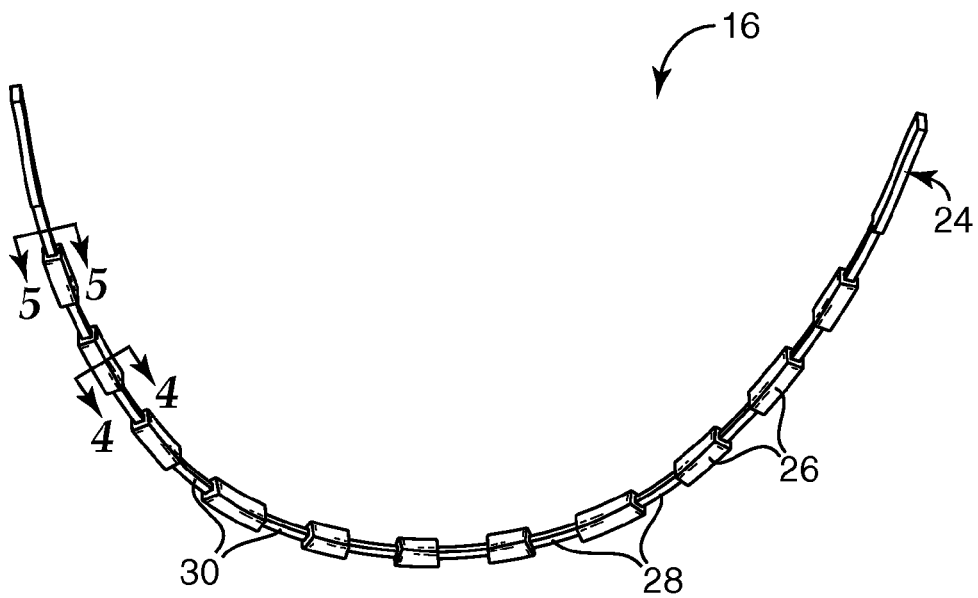
FIG. 3 is a perspective view of the arch member alone that is shown in FIGS. 1 and 2.
Figure 4:
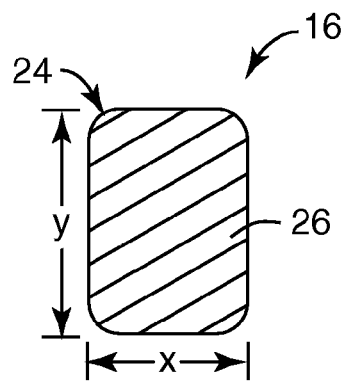
FIG. 4 is an enlarged cross-sectional view taken along line 4-4 of FIG. 3.
Figure 5:
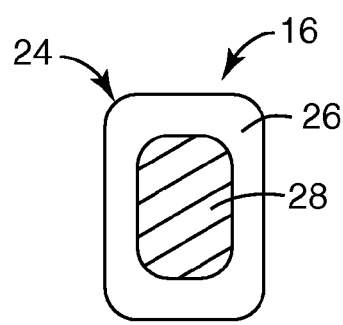
FIG. 5 is an enlarged cross-sectional view taken along lines 5-5 of FIG. 3.

The arch member 16 is shown alone in FIGS. 3-5. The arch member 16 includes an elongated body 24 that is made of a resilient material and has an overall, generally "U"-shaped configuration in plan view. Optionally, the body 24 when relaxed extends along a reference plane that is parallel to the desired occlusal plane of the patient.

As depicted in FIG. 3, the body 24 includes a series of enlarged sections 26 that are connected together by narrowed sections 28. Such construction presents a series of notches 30 that are spaced along the length of the body 24. Each notch 30 extends inwardly from an outer edge of the arch member 16 in a direction toward the curved, central longitudinal axis of the arch member 16.

In the illustrated embodiment, the notches 30 are located along an occlusal edge (i.e., an edge facing the outer tips of the patient's teeth) of the arch member 16 as well as along a gingival edge (i.e., an edge facing the gums or gingiva of the patient) of the arch member 16. However, other constructions are also possible. For example, the narrowed sections 28 could be located along the occlusal edge of the arch member 16 such that the notches 30 are only present along the gingival edge of the arch member 16.

FIG. 4 is an enlarged illustration of a cross-section of one of the enlarged sections 26, taken in a reference plane perpendicular to the curved longitudinal axis of the arch member 16. FIG. 5 is a view somewhat similar to FIG. 4 and is drawn in the same scale as FIG. 4, except that FIG. 5 has been taken across one of the narrowed sections 28. As shown, the cross-sectional area of the enlarged section 26 in FIG. 4 is larger than the cross-sectional area of the narrowed section 28 in FIG. 5.

In this embodiment, the enlarged sections 26 as well as the narrowed sections 28 have a cross-sectional shape that is generally rectangular with rounded corners. However, other constructions are also possible. For example, the cross-sectional shapes of the sections 26, 28 may be elliptical, oval or circular. Combinations of such shapes are also possible. For example, the enlarged sections 26 may have an oval shape in cross-section, while the narrowed sections 28 may have a generally rectangular configuration in cross-section. As used herein, the term "cross-section" means a cross-section that is generally perpendicular to the curved, central longitudinal axis of the arch member 16.

The narrowed sections 28 are received within the archwire slots 20 of the appliances 18. To this end, and in this embodiment, the narrowed sections 28 have an overall size or height in an occlusal-gingival direction that is less than the occlusal-gingival size or height of the archwire slot 20. The narrowed sections 28 also have an overall thickness in a buccolabial-lingual direction that is less than the distance between the bottom or lingual side of the archwire slot 20 and the outer arm portions of the clip 23 so that the clip 23 may close to retain the arch member 16 once the narrowed section 28 is received in the archwire slot 20.

Preferably, the cross-sectional configuration of the narrowed section 28 is complemental to the cross-sectional configuration of the archwire slot 20. For example, the archwire slot 20 has a rectangular shape, and the narrowed section 28 has a matching rectangular shape that is just slightly smaller, such as 0.001 inch or 0.025 mm in height and width. As a result, the narrowed section 28 substantially fills the archwire slot 20 and provides good control over movement of the associated tooth without undue tolerance or "slop". Examples of such tooth movement include torque movements, where the longitudinal axis of the tooth is moved in a rotational direction in a buccolabial-lingual direction, tipping movements, where the tooth is moved such that its longitudinal axis is tipped in a mesial-distal direction, and rotational movement, where the tooth is moved in a rotational direction about its longitudinal axis.

The body 24 has a major cross-sectional axis and a minor cross-sectional axis when considered in reference planes perpendicular to the longitudinal axis of the body 24 and between adjacent notches 30. For example, the enlarged section 26 of the body 24 has a major cross-sectional axis (designated "y") that extends in a generally vertical direction viewing FIG. 4, and a minor cross-sectional axis (designated "x") that extends in a generally horizontal direction viewing FIG. 4. Consequently, the body 24 adjacent the notch 30 (i.e., in areas next to the notch 30 in a occlusal-gingival direction) has an overall size or height in an occlusal-gingival direction that is less than the length of the major cross-sectional axis.

However, the enlarged section 26 of the body 24 need not necessarily have a major cross-sectional axis and a minor cross-sectional axis. Instead, the enlarged section 26 may have a vertical cross-sectional axis and a horizontal cross-sectional axis that are equal in length. For example, the cross-sectional shape of the enlarged section 26 may be square or circular.

In the embodiment illustrated in FIGS. 1-5, the thickness of the body 24 when considered in directions along a buccolabial-lingual reference axis is non-uniform along the length of the body 24, such that the thickness of the enlarged sections 26 is greater than the thickness of the narrowed sections 28. Other constructions are also possible. For example, the enlarged sections 26 may have a thickness that is equal or substantially equal to the thickness of the narrowed sections 28 in directions along a buccolabial-lingual reference axis. In other words, the body 24 adjacent the notch 30 may have an overall size in a buccolabial-lingual direction that is the same as the length of the minor cross-sectional axis.

Figure 5A:
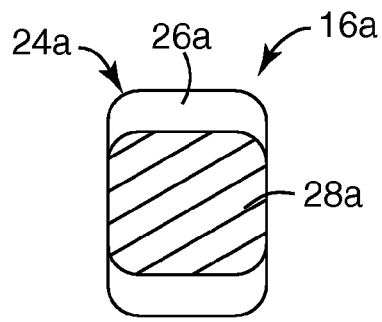
FIG. 5a is a view somewhat similar to FIG. 5 except that the arch member is constructed in accordance with an alternative embodiment of the invention.

FIG. 5a is an enlarged cross-sectional view of an arch member 16a constructed in accordance with an alternative embodiment of the invention. The arch member 16a includes a body 24a with a plurality of narrowed sections 28a. The body 24a also includes a plurality of enlarged sections 26a between the narrowed sections 28a. The enlarged sections 26a are similar in shape to the enlarged section 26 that is illustrated in FIG. 4 in the same scale.

In the embodiment depicted in FIG. 5a, the narrowed section 28a is smaller in height (i.e., in a generally occlusal-gingival direction) than the height of the adjacent enlarged sections. However, the thickness of the narrowed section 28a in a buccolabial-lingual direction is the same as the thickness of the adjacent enlarged sections.

Figure 6:
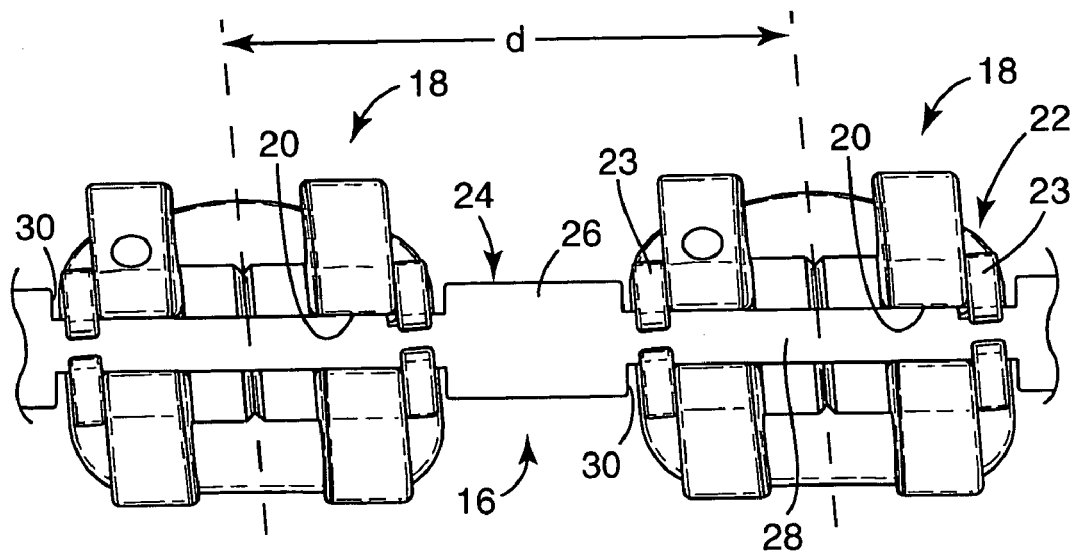
FIG. 6 is an enlarged, fragmentary front elevational view of a portion of the orthodontic brace and the dental arch illustrated in FIGS. 1 and 2.

With reference to FIG. 6, each of the notches 30 has a certain width in a mesial-distal direction (i.e., in directions along the length of the dental arch, or along the length or central axis of the body 24). The width of the notches 30 is at least as great as the length of the corresponding archwire slots 20 (preferably including the space within the clips 23) so that the narrowed sections 28 can be received in the archwire slots 20. Optionally, the width of the notches 30 is greater than the length of the archwire slots 20 in order to enable limited, relative sliding movement of the appliance 18 along the longitudinal axis of the body 24. Alternatively, the width of the notches 30 is substantially equivalent to the length of the archwire slots 20. As an additional option, the width of some of the notches 30 may be substantially equivalent to the length of some of the archwire slots 20, while the width of the remaining notches 30 may be greater than the length of the remaining archwire slots 20. Furthermore, the width of the notches 30 may vary along the length of the arch member 16 in corresponding relation to the variation in width of the respective appliances 18. As is shown in FIG. 6, the enlarged sections 26 are non-coiled and the solid shape of the enlarged sections 26 has a dimension in an occlusal-gingival direction that is greater than the overall occlusal-gingival height of the archwire slot 20.

In instances where the appliances 18 are to be mounted on or near the mesial-distal center of the respective teeth, the centerline spacing between adjacent notches 30 generally corresponds to the centerline distance between corresponding, adjacent teeth 12 of the dental arch 14. Consequently, the centerline spacing between adjacent notches 30 also generally corresponds to the centerline distance between corresponding, adjacent appliances 18 located on the dental arch 14. In FIG. 6, this centerline spacing between adjacent notches 30 is designated by the letter "d" and preferably is identical or substantially identical to the centerline spacing between adjacent teeth 12.

Optionally, the arch member 16 is custom made for a particular patient, and the locations of the notches 30 are determined by measuring the centerline distances between each pair of adjacent teeth in the patient's oral cavity. Alternatively, the arch member 16 for a particular patient is selected from an inventory of pre-manufactured arch members 16 that are constructed according to statistical norms. For instance, a practitioner may determine the best arch member 16 to use from a set of pre-manufactured arch members 16 by measuring the width of each of the patient's teeth and then using a numerical analysis such as a Bolton analysis to facilitate selection of an optimal pre-manufactured arch member 16.

The body 24 of the arch member 16 may be made of any one of a number of suitable materials, including polymeric and metallic materials. Preferred materials include aesthetic polymers such as translucent, transparent or tooth-colored polymers. Examples of suitable polymers include polycarbonates, polyurethanes, silicones, latex, fluoropolymer and polyolefins. Optionally, fibers such as glass fibers can be embedded in the polymeric material. For instance, short fibers having a length equal to the length of the notches 30 may be placed in the narrowed sections 28 and oriented in a mesial-distal direction. As an additional option, one or more metallic wires can be embedded in the polymeric material, and optionally extend along the entire length of the body 24.

As another option, the body 24 may comprise a shape memory polymer such as "Calo-MER" from the Polymer Technical Group, elastic memory composite ("EMC") from Composite Technology Development, Inc. or "Veriflex" from Cornerstone Research Group ("CRG"). As an example, the body 24 may be made using a shape memory polymer such that the arch member 16 has a shape at room temperature that corresponds to the current shape of the patient's teeth. Once the arch member 16 is placed in the patient's oral cavity and the arch member body 24 rises in temperature to a temperature above its glass transition temperature and to a temperature approximating body temperature, the shape memory characteristics of the polymer cause the arch member 16 to move the teeth to desired positions. Such construction facilitates the initial connection of the arch member 22 to the appliance 24, such as in instances where the initial connection is carried out before the arch member 22 approaches body temperature.

As yet another option, the body 24 may be made of a metallic material such as stainless steel, nitinol or a cobalt-based nickel alloy. As one example, the body 24 may have a coiled configuration similar to the shape of a compression spring to facilitate compression of the body 24 in directions along its longitudinal axis. As another example, the body may comprise multiple strands of metallic wires that are braided or twisted together, with openings that are similar to openings of a compression spring to enable compression of the body 24.

Preferably, the arch member 16 is constructed such that the resiliency of the material of the body 24 provides the desired tooth movement without substantial need for relative sliding movement between the arch member 16 and the appliances 18. For example, the arch member 16 may be constructed so that its shape when relaxed corresponds to the desired shape of the dental arch 14 when all of the teeth 12 have been moved to their intended positions, with the notches 30 being arranged to properly locate each tooth 12 at desired final positions along the dental arch 14. This construction helps to avoid problems that are normally associated with the sliding mechanics observed between conventional archwires and orthodontic appliances, such as friction, bending of the archwire, gouging of the archwire and the like.

The arch member 16 of the present invention may be provided as part of a set of similar arch members that are intended for use during different stages of an orthodontic treatment program for a particular patient. For example, the stiffness of the arch members in the set may vary such that the arch members used in the later stages of treatment are stiffer than the arch members used in the earlier stages of treatment. The variation in stiffness may be provided by changing the composition of the arch member, by changing the processing methods used to make the arch member, by changing the shape of the arch member, or by any combination of the foregoing as well as by other methods as well.

Preferably, the arch member 16 and/or the appliances 18 are constructed so that each tooth 12 is in a proper "in/out" position at the conclusion of treatment. "In/out", as used herein, refers to the position of the tooth 12 in a buccolabial-lingual direction (i.e., in directions along a reference axis that extends between the patient's lips or cheeks and the patient's tongue).

As can be appreciated, the present invention provides a significant advantage in that the cross-sectional shape of the arch member 16 need not be constrained to the cross-sectional shape of the archwire slots 20. As a consequence, the arch member may be made of materials that might be otherwise unsatisfactory when constructed in the shape of a conventional archwire. Preferably, the arch member 16 is made of a material that is resistant to staining by foods and beverages.

The embodiments described above and shown in the accompanying drawings are intended to exemplify the invention, and a number of other options are also possible. For example, the appliances 18 may be made of plastic or ceramic materials instead of metal. Additionally, other types of couplings may be used to secure the arch member 16 to the appliances 18. For example, hook and loop couplings may be used, with a hook or loop on the appliance 18 and a loop or hook on the arch member 16, to facilitate attachment and detachment of the arch member 16 from the appliances 18. Snap-on couplings may also be employed, such as appliances with button heads that snap into receptacles of the arch member as described in applicant's co-pending U.S. patent application entitled "Orthodontic Brace with Polymeric Arch Member", Publication No. 05-0277084 and expressly incorporated by reference herein. Furthermore, appliances having archwire slots larger in cross-sectional dimension than the archwire slots of conventional appliances may be employed, in order to take better advantage of the resiliency and inherent memory of certain arch member materials such as polymeric materials. Accordingly, the invention should not be deemed limited to the specific embodiments that are described in detail above, but instead only by a fair scope of the claims that follow.

The invention claimed is:

1. A brace for an orthodontic patient comprising:

a set of orthodontic appliances, each appliance having an archwire slot and constructed for connection to a tooth of the patient's dental arch; and an arch member comprising an elongated polymeric body with an overall, generally "U"-shaped configuration, wherein the body has a plurality of non-coiled enlarged sections and a plurality of narrowed sections that present a plurality of notches that are spaced apart from each other along the length of the body, and wherein the appliances are coupled to the body in locations corresponding to the notches such that each notch receives a corresponding appliance, wherein the enlarged sections have a solid cross-sectional shape, the solid shape having a dimension in an occlusal-gingival direction that is greater than the overall occlusal-gingival height of the archwire slots of the appliances.

2. A brace for an orthodontic patient according to claim 1 wherein the centerline spacing between adjacent notches is generally equivalent to the centerline spacing between corresponding, adjacent appliances.

3. A brace for an orthodontic patient according to claim 1 wherein the slot of each appliance has a certain length in a mesial-distal direction, and wherein each notch has a width in a mesial-distal direction that is at least as great as the certain length of the archwire slot of the corresponding appliance.

4. A brace for an orthodontic patient according to claim 3 wherein the width of the notch is larger than the certain length of the slot of the corresponding appliance in order to enable limited, sliding relative movement of the appliance in directions along the longitudinal axis of the body.

5. A brace for an orthodontic patient according to claim 1 wherein the body has a major cross-sectional axis and a minor cross-sectional axis when considered in reference planes perpendicular to the longitudinal axis of the body and between adjacent notches, and wherein the major cross-sectional axis generally extends in an occlusal-gingival direction and wherein the minor cross-sectional axis generally extends in a buccolabial-lingual direction.

6. A brace for an orthodontic patient according to claim 5 wherein the body adjacent the notch has an overall size in a buccolabial-lingual direction that is less than the length of the minor cross-sectional axis.

7. A brace for an orthodontic patient according to claim 1 wherein the body has a generally rectangular configuration in reference planes perpendicular to the longitudinal axis of the body.

8. A brace for an orthodontic patient according to claim 1 wherein the body is made of a resilient material, and wherein the configuration of the body when relaxed corresponds to a desired configuration of the dental arch at the conclusion of orthodontic treatment.

9. A brace for an orthodontic patient according to claim 1 wherein the body is made of a resilient material, and wherein the configuration of the body when relaxed corresponds to a desired configuration of the dental arch at an intermediate stage of orthodontic treatment.

10. A brace for an orthodontic patient according to claim 1 wherein the body comprises a memory material.

* * * * *

UNITED STATES PATENT AND TRADEMARK OFFICE
CERTIFICATE OF CORRECTION

| | | |
|---|---|---|
| PATENT NO. | : 7,252,506 B2 | Page 1 of 1 |
| APPLICATION NO. | : 10/865148 | |
| DATED | : August 7, 2007 | |
| INVENTOR(S) | : Ming-Lai Lai | |

It is certified that error appears in the above-identified patent and that said Letters Patent is hereby corrected as shown below:

Column 10
Line 5, In Claim 10, after "comprises a" insert --shape--.

Signed and Sealed this

Sixth Day of November, 2007

JON W. DUDAS
*Director of the United States Patent and Trademark Office*